US012668399B2

(12) United States Patent
Maury et al.

(10) Patent No.: US 12,668,399 B2
(45) Date of Patent: Jun. 30, 2026

(54) NEST FOR THE PACKAGING OF PLUNGER STOPPERS WITH STACKING PINS ENSURING A RELIABLE ALIGNMENT OF A PILE OF NESTS

(71) Applicant: Becton Dickinson France, Le Pont-de-Claix (FR)

(72) Inventors: Camille Maury, Grenoble (FR); Gildas Esnault, Grenoble (FR); Gwenn Le Dimet, Charavines (FR)

(73) Assignee: Becton Dickinson France, Le Pont de Claix (FR)

( * ) Notice: Subject to any disclaimer, the term of this patent is extended or adjusted under 35 U.S.C. 154(b) by 54 days.

(21) Appl. No.: 18/273,591

(22) PCT Filed: Jan. 26, 2022

(86) PCT No.: PCT/EP2022/051734
§ 371 (c)(1),
(2) Date: Jul. 21, 2023

(87) PCT Pub. No.: WO2022/161992
PCT Pub. Date: Aug. 4, 2022

(65) Prior Publication Data
US 2024/0067396 A1     Feb. 29, 2024

(30) Foreign Application Priority Data
Jan. 26, 2021     (EP) ..................................... 21305101

(51) Int. Cl.
*B65D 21/02* (2006.01)
*A61M 5/00* (2006.01)
*B65D 25/10* (2006.01)

(52) U.S. Cl.
CPC ......... *B65D 21/0215* (2013.01); *A61M 5/008* (2013.01); *B65D 25/108* (2013.01)

(58) Field of Classification Search
CPC .. B65D 21/0215; B65D 25/108; A61M 5/008; B01L 2200/141; B01L 2300/0887; B01L 2400/0487; B01L 9/54; A45D 44/04
(Continued)

(56) References Cited

U.S. PATENT DOCUMENTS

| | | | | | |
|---|---|---|---|---|---|
| 386,674 | A | * | 7/1888 | Wells | B42F 17/08 |
| | | | | | 211/11 |
| 2,916,239 | A | * | 12/1959 | Stopps | B65D 19/385 |
| | | | | | 108/53.5 |

(Continued)

FOREIGN PATENT DOCUMENTS

| | | | |
|---|---|---|---|
| CN | 2880705 Y | * | 3/2007 |
| CN | 111344064 A | | 6/2020 |

(Continued)

*Primary Examiner* — Don M Anderson
*Assistant Examiner* — Justin Caudill
(74) *Attorney, Agent, or Firm* — The Webb Law Firm

(57) ABSTRACT

A nest (10) for the storage of medical device components, including a top surface (12), a bottom surface (14), and a plurality of receptacles (20) for the storage of a plurality of medical device components therein, wherein each of the plurality of receptacles (20) includes a sidewall portion (22) extending downward from the bottom surface (14) of the nest (10). The nest (10) further includes a plurality of openings (26) formed in the top surface (12) and a plurality of stacking pins (28) extending from the bottom surface (14). Each of the plurality of openings (26) is substantially aligned with a respective one of the plurality of stacking pins (28) so as to enable two or more nests (10) to be stacked vertically relative to one another via association between the openings (26) and the stacking pins (28).

14 Claims, 4 Drawing Sheets

(58) Field of Classification Search
USPC .......................................................... 206/511
See application file for complete search history.

(56) References Cited

U.S. PATENT DOCUMENTS

| | | | | |
|---|---|---|---|---|
| 3,420,402 | A * | 1/1969 | Frater | B65D 21/045 |
| | | | | 206/520 |
| 3,734,341 | A * | 5/1973 | Levenhagen | B65D 21/045 |
| | | | | 211/126.7 |
| 5,035,326 | A * | 7/1991 | Stahl | B65D 21/041 |
| | | | | 206/505 |
| 5,752,602 | A * | 5/1998 | Ackermann | B65D 21/046 |
| | | | | 206/505 |
| 6,250,052 | B1 | 6/2001 | Porfano et al. | |
| 6,752,967 | B2 * | 6/2004 | Farina | B01L 3/5085 |
| | | | | 206/509 |
| 7,721,891 | B2 * | 5/2010 | Dubois | B65D 21/045 |
| | | | | 206/511 |
| 8,118,167 | B2 * | 2/2012 | Togashi | A61B 50/30 |
| | | | | 206/519 |
| 8,453,838 | B2 | 6/2013 | Hill | |
| 8,485,357 | B2 * | 7/2013 | Song | B01L 9/00 |
| | | | | 211/74 |
| 8,827,075 | B2 * | 9/2014 | Seiwell | A61M 5/008 |
| | | | | 206/443 |
| 9,095,848 | B2 * | 8/2015 | Carrel | B65D 71/70 |
| D804,052 | S * | 11/2017 | Dadachanji | D24/230 |
| 10,124,928 | B2 * | 11/2018 | Wissner | A61J 7/0069 |
| 10,350,347 | B2 * | 7/2019 | Gagnieux | A61M 5/008 |
| 10,434,242 | B2 * | 10/2019 | Thompson | A61M 5/008 |
| 10,874,473 | B2 | 12/2020 | Togashi et al. | |
| 10,918,784 | B2 | 2/2021 | Yoshida | |
| 11,298,455 | B2 * | 4/2022 | Nicolas | A61M 5/008 |
| D951,483 | S * | 5/2022 | Potdar | D24/230 |
| 11,540,892 | B2 | 1/2023 | Yoshida | |
| 2009/0100802 | A1 * | 4/2009 | Bush | A61M 5/002 |
| | | | | 53/434 |
| 2009/0105096 | A1 | 4/2009 | Uematsu et al. | |
| 2011/0192756 | A1 * | 8/2011 | Hill | A61M 5/008 |
| | | | | 206/515 |
| 2012/0080341 | A1 | 4/2012 | Finke et al. | |
| 2013/0161225 | A1 * | 6/2013 | Lepot | B01L 9/54 |
| | | | | 206/557 |
| 2015/0114871 | A1 * | 4/2015 | Fitzpatrick | A61J 1/16 |
| | | | | 206/508 |
| 2016/0121042 | A1 * | 5/2016 | Christensen | A61M 5/002 |
| | | | | 206/366 |
| 2018/0126066 | A1 | 5/2018 | Narvekar et al. | |
| 2019/0070357 | A1 | 3/2019 | Evans et al. | |
| 2019/0083697 | A1 | 3/2019 | Evans et al. | |
| 2019/0125473 | A1 | 5/2019 | Togashi et al. | |
| 2020/0055631 | A1 * | 2/2020 | Combs | B65D 21/0215 |
| 2020/0113315 | A1 * | 4/2020 | Parker | A47F 7/0028 |
| 2021/0178400 | A1 | 6/2021 | Sager et al. | |
| 2021/0212897 | A1 * | 7/2021 | Kloke | A61J 1/16 |
| 2022/0371765 | A1 * | 11/2022 | Hutterer | A61J 1/16 |

FOREIGN PATENT DOCUMENTS

| | | | | |
|---|---|---|---|---|
| DE | 102011104300 A1 * | 9/2012 | ........... | A61M 5/008 |
| EP | 2017624 A1 | 1/2009 | | |
| EP | 2436408 A1 | 4/2012 | | |
| EP | 2476448 A1 * | 7/2012 | ............. | A61M 5/00 |
| EP | 3381828 A1 | 10/2018 | | |
| EP | 3450349 A1 | 3/2019 | | |
| EP | 3524293 A1 | 8/2019 | | |
| EP | 3834943 A1 | 6/2021 | | |
| GB | 1144226 | 3/1969 | | |
| JP | 2019504679 A | 2/2019 | | |
| WO | WO-2017038878 A1 * | 3/2017 | ............... | A61J 1/06 |
| WO | WO-2017170636 A1 * | 10/2017 | ............... | A61J 1/06 |
| WO | 2021009898 A1 | 1/2021 | | |

* cited by examiner

NEST FOR THE PACKAGING OF PLUNGER STOPPERS WITH STACKING PINS ENSURING A RELIABLE ALIGNMENT OF A PILE OF NESTS

CROSS-REFERENCE TO RELATED APPLICATIONS

This application is the United States national phase of International Application No. PCT/EP2022/051734 led Jan. 26, 2022, and claims priority to European Priority Application No. 21305101.4, entitled "A Nest for the Packaging of Plunger Stoppers with Stacking Pins Ensuring A Reliable Alignment of a Pile of Nests", filed Jan. 26, 2021, the entire disclosures of which are hereby incorporated by reference in their entirety.

BACKGROUND

Field of the Disclosure

The present disclosure relates generally to nest arrangements for the packaging of plunger stoppers used in medical devices such as, e.g., syringes. More particularly, the present disclosure relates to nest arrangements utilizing stacking pins so as to ensure reliable alignment of a pile (or stack) of nests positioned vertically atop one another.

Description of the Related Art

As is known in the art, transfer or storage devices for delivery or storage of a medicament, drug, or vaccine (such as, e.g., syringes) utilize a plunger stopper in contact with an inside surface of a generally tubular syringe barrel in order to draw a substance into (or expel a substance from) the device by way of a plunger rod.

Currently, many such devices are filled and assembled using automated filling machines. Not only do such machines improve productivity and accuracy, but they also provide for a substantially sterile and aseptic filling environment. The various components of the devices (e.g., plunger stoppers, syringe barrels, etc.) are separately provided within the filling machines to enable at least some level of automated assembly.

Typically, a plurality of plunger stoppers are provided in bags or in nests (which are also provided in bags) to be accessed by the filling machine during assembly. Conversely, the syringe barrels are generally packaged in nests having numerous "chimneys" formed therein to hold the barrels, with each nest configured to be held within a tub when introduced into the filling machine.

While the current nests for syringe barrels are specifically designed for use with tubs, the current nests designed for holding plunger stoppers are not configured for use with a specific tub profile, nor do they fit securely within the tubs used for syringe barrels. In some automated filling machines, the lack of a tub for holding the nests of plunger stoppers does not present an issue. However, in other, more recently-designed filling equipment (such as, e.g., the Vanrx SA25 robotic aseptic filling workcell from Vanrx Pharmasystems Inc.), only components packaged in both nests and tubs are capable of being handled.

Furthermore, as noted above, currently-available nests for plunger stoppers are not designed to be held within existing tub designs, nor are their nests configured for plunger stoppers which are consistently stackable. Thus, if one were to attempt to utilize existing nests and tubs together in relation to plunger stoppers, the combination may result in unreliable positioning and unwanted movement of the nests within the tub and/or relative to nests above or below when stacked, which would be problematic for the robotic handling of the nests within the filling equipment. Documents EP3450349A1, EP3834943A1, EP3524293A1 and EP2017624A1 relate to packaging for containers.

SUMMARY

In view of the foregoing, there exists a need for a nest designed specifically for plunger stoppers, as well as a nest designed to ensure consistent and secure alignment of nests when vertically stacked either within or outside of a tub.

Embodiments of the present disclosure are directed to a nest for the storage of medical device components. The nest includes a top surface, a bottom surface, and a plurality of receptacles for the storage of a plurality of medical device components therein, wherein each of the plurality of receptacles includes a sidewall portion extending downward from the bottom surface of the nest. The nest further includes a plurality of openings formed in the top surface and a plurality of stacking pins extending from the bottom surface, wherein each of the plurality of openings is substantially aligned with a respective one of the plurality of stacking pins so as to enable two or more nests to be stacked vertically relative to one another via association between the openings and the stacking pins.

In some embodiments, each stacking pin includes an upper portion and a lower portion, and the lower is sized to be smaller than the upper portion.

In some embodiments, the lower portion of each of the stacking pins and each of the plurality of openings are substantially cylindrical.

In some embodiments, an exterior diameter of the lower portion of each of the stacking pins is smaller than an internal diameter of each of the plurality of openings.

In some embodiments, the lower portion of each stacking pin of a first nest is configured to fit within a respective opening of a second nest when the first and second nests are stacked vertically relative to one another.

In some embodiments, the lower portion of each of the stacking pins is formed of a different material than the upper portion of each of the stacking pins.

In some embodiments, each stacking pin includes a pin bottom surface and each of the plurality of receptacles includes a receptacle bottom surface, and the pin bottom surface extends farther below the bottom surface of the nest than the receptacle bottom surface.

In some embodiments, when at least two nests are stacked vertically relative to one another, the sidewall portion of each of the plurality of receptacles of the nest at an upper position does not contact the nest at a lower position.

In some embodiments, the nest is substantially quadrilateral in shape.

In some embodiments, the plurality of openings and the plurality of stacking pins are positioned proximate to respective corners of the nest.

In some embodiments, the plurality of openings includes at least three openings, and the plurality of stacking pins includes at least three stacking pins.

In some embodiments, each of the plurality of openings has a depth that is less than an overall thickness of the nest between the top surface and the bottom surface.

In some embodiments, at least one finger opening is formed in the nest.

In some embodiments, the nest further includes a flange extending at least partially around each finger opening and extending from the bottom surface of the nest.

In some embodiments, the nest is formed of polypropylene.

Further details and advantages of the present disclosure will be understood from the following detailed description read in conjunction with the accompanying drawings.

DESCRIPTION OF THE INVENTION

Figure 1:
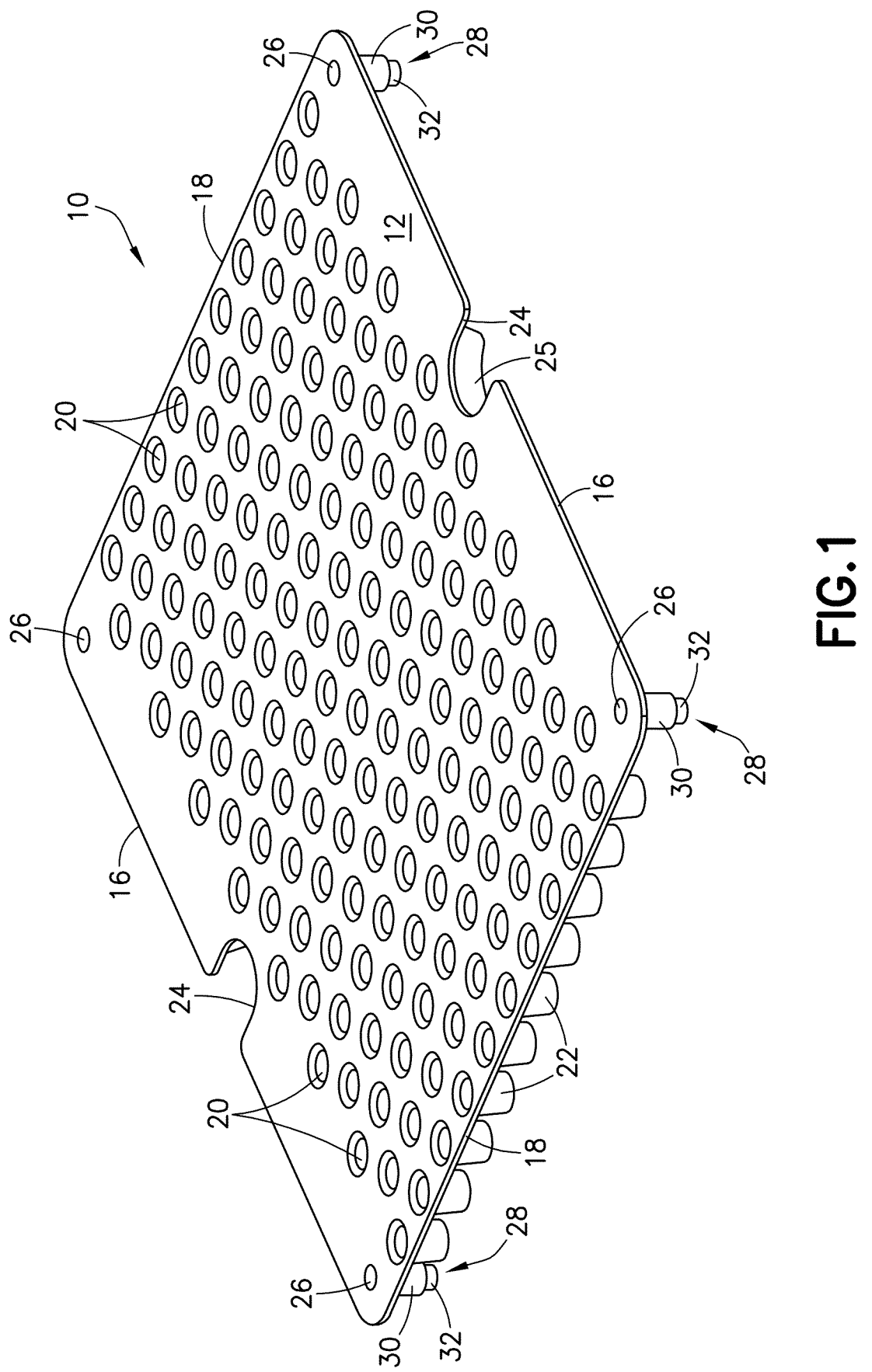
FIG. 1 is a top isometric view of a nest for the storage of plunger stoppers in accordance with an aspect of the present disclosure.

The following description is provided to enable those skilled in the art to make and use the described aspects contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For the purposes of the description hereinafter, the terms "upper", "lower", "right", "left", "vertical", "horizontal", "top", "bottom", "lateral", "longitudinal", and derivatives thereof shall relate to the invention as it is oriented in the drawings. However, it is to be understood that the invention may assume various alternative variations, except where expressly specified to the contrary. It is also to be understood that the specific devices illustrated in the attached drawings, and described in the following specification, are simply exemplary aspects of the invention. Hence, specific dimensions and other physical characteristics related to the aspects disclosed herein are not to be considered as limiting.

Figure 2:
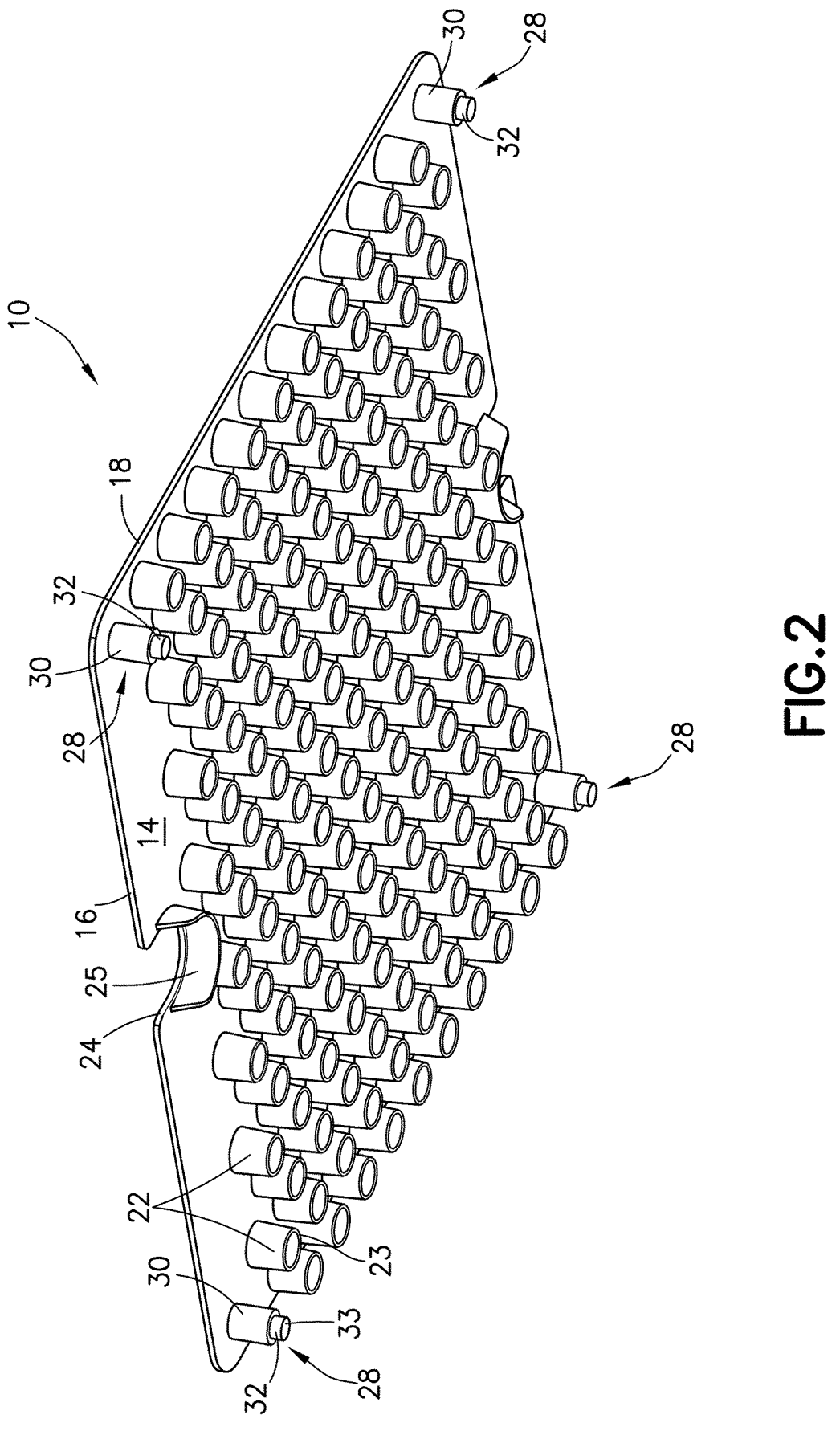
FIG. 2 is a bottom isometric view of the nest of FIG. 1.
Figure 3:
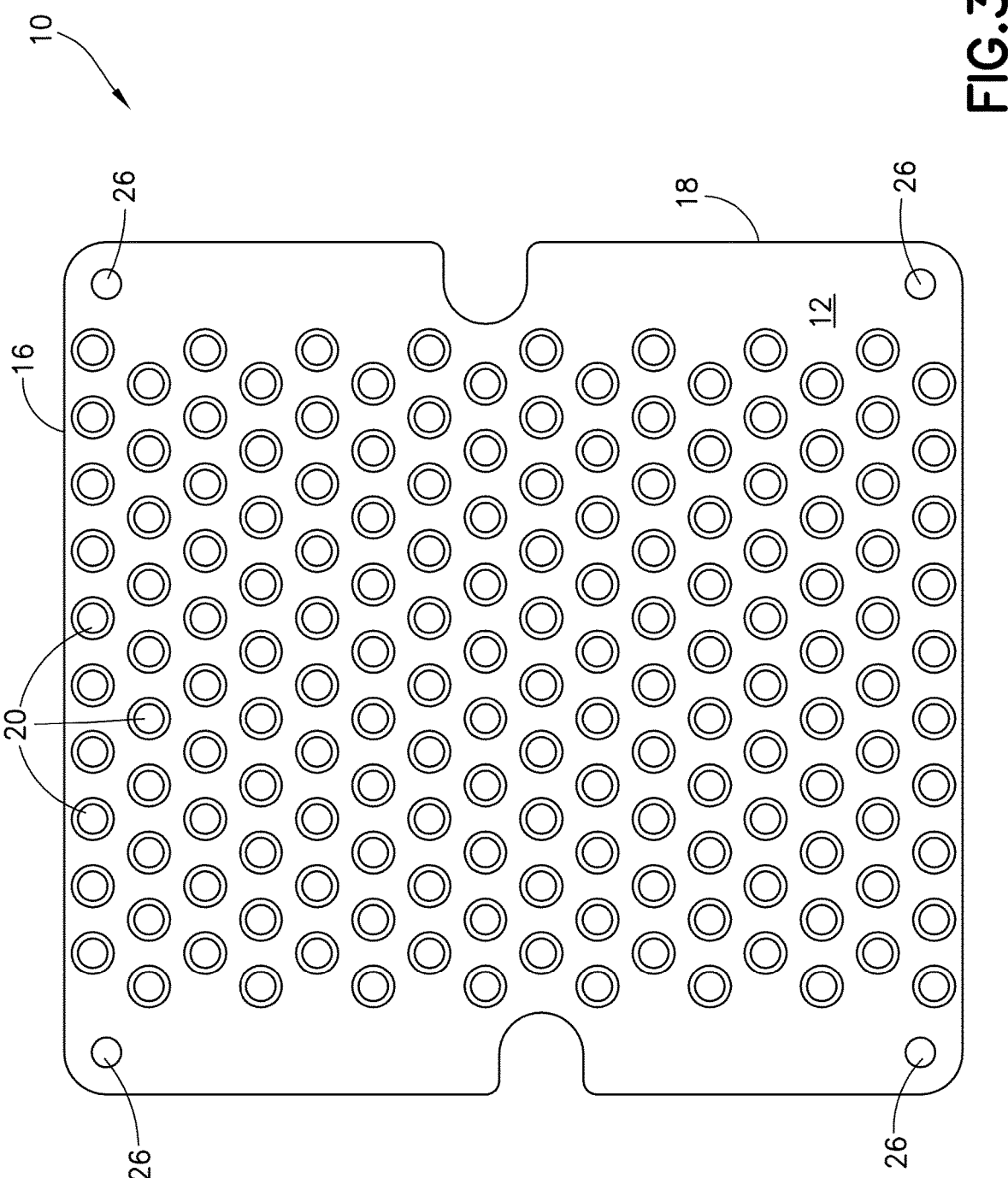
FIG. 3 is a top plan view of the nest of FIG. 1.

Referring to FIGS. 1-3, a nest 10 in accordance with an aspect of the present disclosure is shown. Each nest 10 is configured to store a plurality of plunger stoppers (not shown) in a way that provides for desired positioning and alignment of both the plunger stoppers and nest(s) to allow for accurate handling by the robotic components of the automated filling machines. While not shown, a plurality of nests 10 are capable of being removably retained within a tub or other holding arrangement, with the nests 10 configured to be stackable vertically atop one another, as will be described in further detail below. Typically, between two and ten nests may be vertically stacked relative to one other. For example, in some embodiments, at least two nests are stacked onto each other. In one embodiment, the tub is configured such that seven nests may be stacked onto each other. Additionally, it is to be understood that the nests described in the present disclosure are not limited to use with plunger stoppers, and may be utilized with other elements and/or devices, such as, e.g., needle covers, tip caps, or any other medical components.

Each nest 10 includes a plurality of stopper receptacles 20 formed therein. The stopper receptacles 20 may be formed as substantially frustoconical "chimneys", each capable of holding a plunger stopper therein for access and removal by, e.g., components of an autonomous filling machine. Referring to FIGS. 1 and 2, each stopper receptacle 20 includes an upper opening formed in a top surface 12 of the nest 10, while the "chimney" of the stopper receptacle 20 is formed by a substantially frustoconical wall portion 22 which extends below a bottom surface 14 of the nest 10. The diameter and size of each stopper receptacle 20 may vary based on the type of stopper utilized during a particular filling operation. In one embodiment, the nest 10 may be configured to retain, e.g., 160 stoppers sized for use in a 1 mL syringe. However, it is to be understood that the nest 10 may be configured to hold more or fewer stoppers, as well as stoppers of differing size(s). For example, a nest 10 in accordance with another embodiment may be configured to hold 100 stoppers sized for use with a 2.25 mL syringe. Thus, in some embodiments, the overall number and positioning of stopper receptacles 20 may vary as compared to that which is shown in FIGS. 1 and 2.

The nest 10 includes a pair of long sides 16 and a pair of short sides 18. However, in alternative embodiments, it is to be understood that the sides of nest 10 need not be different in length and/or parallel, and may instead be, e.g., equal, non-parallel, etc. The general dimensions of each nest 10 (i.e., length, width, and height) may be adapted based on the specific holding tub or automated filling machine being utilized.

As shown in FIGS. 1 and 2, the long sides 16 may each include a finger opening 24 formed thereon, wherein each finger opening 24 is designed to enable simplified manual loading (and/or removal) of the nest 10 into (or from), e.g., a tub or other holding arrangement. In some embodiments, a flange 25 may at least partially surround each finger opening 24 and extend from the bottom surface 14 of nest 10, thereby providing the user with a larger surface area upon which to grip the nest 10. While two finger openings 24 are shown on opposing long sides 16 in FIGS. 1 and 2, it is to be understood that nest 10 may include more or fewer finger openings, either on long sides 16 or the short sides 18. Additionally, in some embodiments, the finger openings 24 may be omitted altogether.

Referring to FIGS. 1-4, the nest 10 in accordance with the present disclosure includes a plurality of openings 26 formed within the top surface 12 proximate the respective corners of the nest 10. In some embodiments, each opening 26 may be substantially cylindrical in shape, and has a depth that is less than the overall thickness of the nest 10 between the top surface 12 and the bottom surface 14. However, in other embodiments, each opening 26 may extend entirely through the nest 10.

Additionally, the nest 10 in accordance with the present disclosure includes a plurality of stacking pins 28. The stacking pins 28 extend from the bottom surface 14 of the nest 10, and are positioned substantially in-line with the openings 26. In one embodiment, each stacking pin 28 is at least partially cylindrical in shape, and includes an upper portion 30 and a lower portion 32, with lower portion 32 being smaller in diameter than upper portion 30. However, in some embodiments, each stacking pin 28 may have a consistent diameter along its entire length. Furthermore, in some embodiments, at least a portion of stacking pin 28 may be non-cylindrical shape. For example, in some embodiments, at least the lower portion 32 may be frustoconical, thereby tapering slightly toward a distal end of the stacking pin 28.

As will be described in further detail below, the positional relationship between the openings 26 and the stacking pins 28 is configured to aid in the relative alignment of multiple nests 10 when vertically stacked atop one another. The stacking pins 28 are sized and configured so as to resist the dislodgement of stacked nests 10 due to slight lateral and/or vertical forces being applied to the nests 10, yet still allow for the vertical separation of nests 10, when desired.

Figure 4:
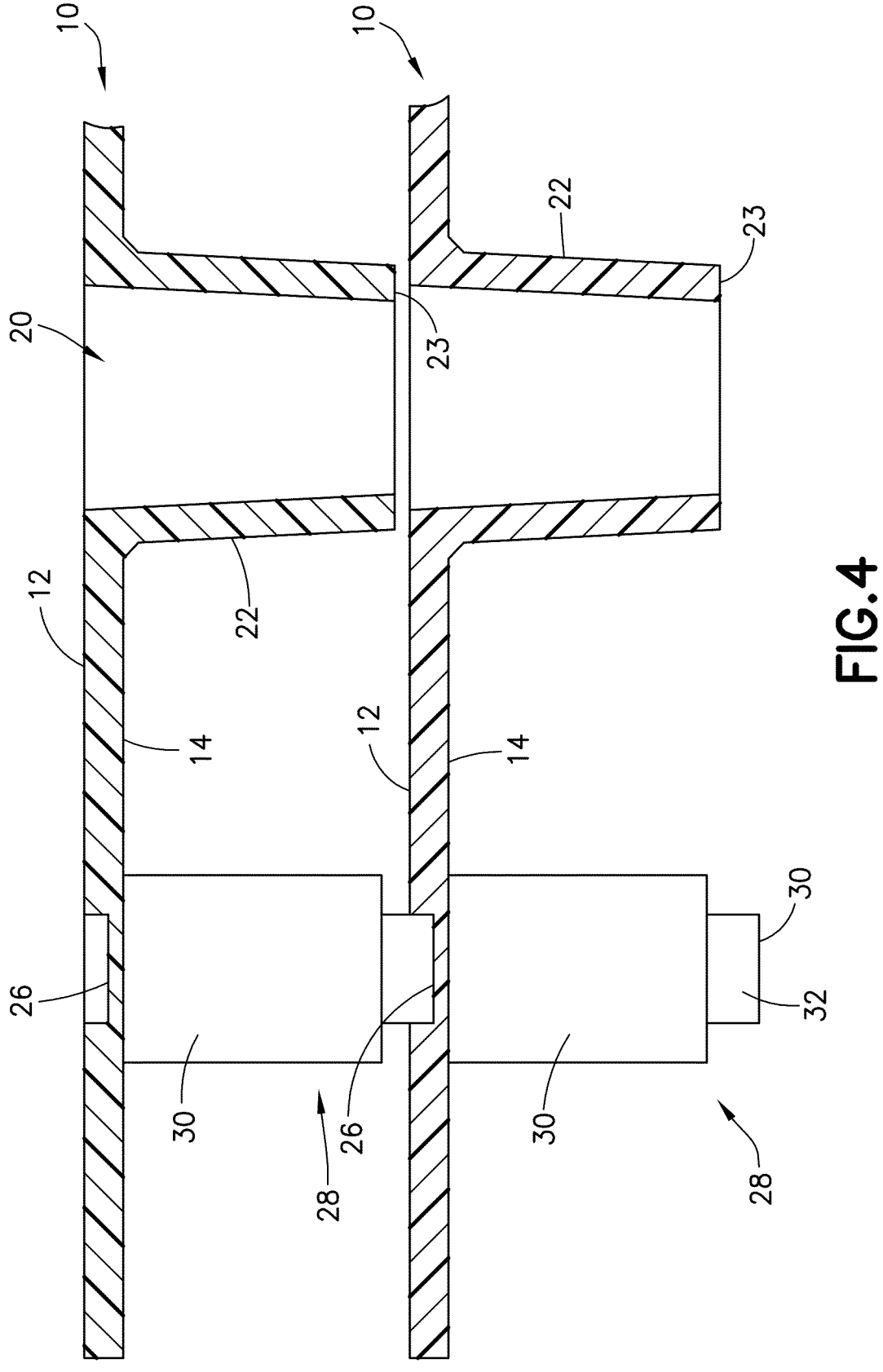
FIG. 4 is a partial cross-sectional side view of a pair of stacked nests in accordance with an aspect of the present disclosure.

Referring to FIGS. 2 and 4, the lower portion 32 of each stacking pin 28 includes a pin bottom surface 33, while the frustoconical wall portion 22 of each stopper receptacle 20 includes a receptacle bottom surface 23. As is shown in FIG. 4, the pin bottom surface 33 of each stacking pin 28 is configured to extend a greater distance below the bottom surface 14 of the nest 10 than the receptacle bottom surface 23. For example, the receptacle bottom surface 23 may extend between 7-12 mm below the bottom surface 14 of the nest 10, while the pin bottom surface 33 may extend, e.g., 1-3 mm farther below the bottom surface 14 than the receptacle bottom surface 23.

Accordingly, as is shown in FIG. 4, when two (or more) nests 10 are stacked relative to one another, the bottom portion 32 of each stacking pin 28 extending from an upper nest 10 is configured to fit within a respective opening 26 of a lower nest 10, while the frustoconical wall portion 22 of each stopper receptacle 20 of the upper nest 10 remains out of contact with the frustoconical wall portion 22 of the stopper receptacles 20 of the lower nest 10. In this way, the association between the openings 26 and the stacking pins 28 alone is configured to ensure the proper alignment and retention of stacked nests 10 relative to one another.

Referring still to FIG. 4, in one embodiment, the bottom portion 32 of each stacking pin 28 may be sized and configured so as to substantially fit within a corresponding opening 26 of a nest 10 positioned therebelow. An exterior diameter of the bottom portion 32 of each stacking pin 28 may be sized and configured to be slightly smaller than an interior diameter of the openings 26, while a height of each bottom portion 32 may be slightly taller than a depth of the openings 26. In this way, the bottom portion 32 of each stacking pin 28 may fit within a respective opening 26 such that a minimal amount of "play" (i.e., lateral movement) between the bottom portion 32 and respective opening 26 is allowed, thereby preventing the stacking pins 28 from becoming from stuck within the openings 26. With such a configuration, two or more stacked nests 10 are capable of resisting dislodgement due to minimal horizontal or vertical movement, but are able to be separated by a filling machine and/or user, when desired.

In the embodiment shown in FIGS. 1-4, each nest 10 is shown as including four openings 26 and four stacking pins 28, with each being positioned proximate the respective corners of nest 10. However, it is to be understood that more or fewer openings 26 and/or stacking pins 28 may be utilized in accordance with the present disclosure. For example, in an alternative embodiment, each nest 10 may include only three openings 26 and three stacking pins 28. Furthermore, the positioning of the openings 26 and/or stacking pins 28 is not limited to the corner regions of the nests 10, and may be, e.g., positioned along the lateral sides of the nests 10, in the central region of the nests 10, etc. Additionally, while nest 10 is shown as being quadrilateral in shape in FIGS. 1-3, it is to be understood that nest 10 is not limited as such and may be formed in any appropriate shape and/or size.

Each nest 10 may be formed of any suitable material, and via any suitable method. For example, a nest 10 may be formed of, e.g., a plastic, polymer (e.g., polypropylene), metal, etc., and may be formed by, e.g., molding, stamping, thermoforming, extrusion, welding, etc. Furthermore, a nest 10 may be formed as a single piece, or as multiple pieces coupled together. If formed of multiple pieces, the materials forming each piece may be the same or different.

Additionally and/or alternatively, each stacking pin 28 may be formed unitarily with the nest 10 by way of, e.g., molding, stamping, thermoforming, etc. However, in another embodiment, each stacking pin 28 may be formed separately such that the stacking pins 28 are subsequently affixed to the nest 10 via any appropriate method such as, e.g., an adhesive, welding, one or more fasteners, etc.

Additionally and/or alternatively, the top portion 30 and bottom portion 32 of each stacking pin 28 may be formed of the same or different materials. For example, in some embodiments, the bottom portion 32 may be formed of a material having increased hardness and/or wear-resistance characteristics as compared the top portion 30. As the bottom portion 32 is the portion of stacking pin 28 which contacts and/or fits within an opening 26 of another nest 10, having such an increased hardness and/or wear-resistance may be beneficial in, e.g., prolonging the life of the nests 10, ensuring a consistent and smooth association between the stacking pin 28 and the opening 26, etc.

Furthermore, the openings 26 may be formed by way of any appropriate method such as, e.g., molding, stamping, machining, drilling, etc. Additionally, in some embodiment, the openings 26 may be reinforced with a material and/or coating so as to increase the hardness and/or wear-resistance of an interior contact surface of each opening 26. As with the stacking pin 28 described above, such an increased hardness and/or wear-resistance of the opening(s) 26 may be beneficial in, e.g., prolonging the life of the nests 10, ensuring a consistent and smooth association between the stacking pin 28 and the opening 26, etc.

While several embodiments of nests and nest arrangements are shown in the accompanying figures and described hereinabove in detail, other embodiments will be apparent to, and readily made by, those skilled in the art without departing from the scope and spirit of the invention. For example, it is to be understood that this disclosure contemplates, to the extent possible, that one or more features of any embodiment can be combined with one or more features of any other embodiment. Accordingly, the foregoing description is intended to be illustrative rather than restrictive.

What is claimed is:

1. A nest for the storage of medical device components, comprising:
   a top surface,
   a bottom surface,
   a plurality of receptacles for the storage of a plurality of medical device components therein, wherein each of the plurality of receptacles comprises a sidewall portion extending downward from the bottom surface of the nest,
   wherein the nest further comprises a finger opening formed therein, a plurality of openings formed in the top surface, each of the plurality of openings are positioned proximate to corners of the nest, each of the plurality of openings has a depth that is less than an overall thickness of the nest between the top surface and the bottom surface, and a plurality of stacking pins downwardly extending from the bottom surface, wherein each of the plurality of openings is substantially aligned with a respective one of the plurality of stacking pins so as to enable two or more nests to be stacked vertically relative to one another via association between the openings and the stacking pins, wherein a lower portion of each of the stacking pins is formed of a different material than an upper portion of each of the stacking pins, the lower portion having a diameter smaller than a diameter of the upper portion and the lower portion having a shorter length than a length of the upper portion, wherein at least a portion of the plurality of receptacles is provided between at least two of the plurality of openings, and the finger opening is provided between at least two of the plurality of openings.

2. The nest according to claim 1, wherein the lower portion of each of the stacking pins and each of the plurality of openings are substantially cylindrical.

3. The nest according to claim 2, wherein an exterior diameter of the lower portion of each of the stacking pins is smaller than an internal diameter of each of the plurality of openings.

4. The nest according to claim 1, wherein the lower portion of each stacking pin of a first nest is configured to fit within a respective opening of a second nest when the first and second nests are stacked vertically relative to one another.

5. The nest according to claim 1, wherein each stacking pin comprises a pin bottom surface and each of the plurality of receptacles comprises a receptacle bottom surface, and wherein the pin bottom surface extends farther below the bottom surface of the nest than the receptacle bottom surface.

6. The nest according to claim 1, wherein when at least two nests are stacked vertically relative to one another, the sidewall portion of each of the plurality of receptacles of the nest at an upper position does not contact the nest at a lower position.

7. The nest according to claim 1, wherein the nest is substantially quadrilateral in shape.

8. The nest according to claim 1, wherein the plurality of stacking pins are positioned proximate to respective corners of the nest.

9. The nest according to claim 1, wherein the plurality of openings comprises at least three openings, and wherein the plurality of stacking pins comprises at least three stacking pins.

10. The nest according to claim 1, further comprising a flange extending at least partially around each finger opening and extending from the bottom surface of the nest.

11. The nest according to claim 1, wherein the nest is formed of polypropylene.

12. A nest for the storage of medical device components, comprising:

a top surface, a bottom surface, a plurality of receptacles for the storage of a plurality of medical device components therein, wherein each of the plurality of receptacles comprises a sidewall portion extending downward from the bottom surface of the nest, wherein the nest further comprises a finger opening formed therein, a plurality of openings formed in the top surface, each of the plurality of openings are positioned proximate to corners of the nest, each of the plurality of openings has a depth that is less than an overall thickness of the nest between the top surface and the bottom surface, and a plurality of stacking pins downwardly extending from the bottom surface, wherein each of the plurality of openings is substantially aligned with a respective one of the plurality of stacking pins so as to enable two or more nests to be stacked vertically relative to one another via association between the openings and the stacking pins, wherein a lower portion of each of the stacking pins is formed of a different material than an upper portion of each of the stacking pins, the lower portion having a diameter smaller than a diameter of the upper portion and the lower portion having a shorter length than a length of the upper portion, wherein at least a portion of the plurality of receptacles is provided between at least two of the plurality of openings, and the finger opening is provided between at least two of the plurality of openings, wherein when at least two nests are stacked vertically relative to one another, the stacking pins are configured to separate the at least two nests such that the sidewall portion of each of the plurality of receptacles of the nest at an upper position does not contact the nest at a lower position.

13. The nest according to claim 1, wherein the plurality of stacking pins extends further downward than the sidewall portion of the plurality of receptacles such that the plurality of receptacles are spaced from a top surface of the two or more nests.

14. The nest according to claim 12, wherein the plurality of stacking pins extends further downward than the sidewall portion of the plurality of receptacles such that the plurality of receptacles are spaced from a top surface of the two or more nests.

* * * * *